United States Patent
Sacchettini

[19]
[11] Patent Number: 5,882,878
[45] Date of Patent: *Mar. 16, 1999

[54] INHA CRYSTALS AND THREE DIMENSIONAL STRUCTURE

[75] Inventor: James Sacchettini, New Rochelle, N.Y.

[73] Assignee: Albert Einstein College of Medicine of Yeshiva University, Bronx, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 701,062

[22] Filed: Aug. 21, 1996

Related U.S. Application Data

[62] Division of Ser. No. 491,146, Jun. 16, 1995, Pat. No. 5,556,778, which is a continuation of Ser. No. 307,376, Sep. 16, 1994, abandoned, which is a continuation-in-part of Ser. No. 234,011, Apr. 28, 1994, Pat. No. 5,702,935.

[51] Int. Cl.$^6$ ..................................................... C12Q 1/26
[52] U.S. Cl. .............................. 435/25; 435/26; 435/189; 536/23.2; 536/23.7
[58] Field of Search ............................... 435/189, 25, 26; 536/23.2, 23.7

[56] References Cited

U.S. PATENT DOCUMENTS

| | | | |
|---|---|---|---|
| 4,886,646 | 12/1989 | Carter et al. | 117/202 |
| 4,919,899 | 4/1990 | Herrmann et al. | 422/245.1 |
| 4,990,216 | 2/1991 | Fujita et al. | 117/68 |

OTHER PUBLICATIONS

Lefford, *Tubercle* vol. 47, p. 198 (1966).
Hok, *Am. Rev. Respir. Rev.*, vol. 90, pp. 468–469 (1964).
Banerjee et al., *Science*, vol. 263, pp. 227, 230 (Jan. 1994).
Zhang et al., *Molec. Microbiol.*, vol. 8, pp. 521–529 (1993).
Canetti, *Am. Rev. Respir. Dis.*, vol. 92, p. 687 (1965).
Banerjee et al. (1994) *Science*, 263, "inhA, a Gene Encoding a Target for Isoniazid and Ethionamide in *Mycobacterium tuberculosis*", pp. 227–230.
Dessen et al. (1995) *Science*, 267, "Crystal Structure and function of the Isoniazid Target of *Mycobacterium tuberculosis* ", pp. 1638–1641.
McPherson (1976) *Meth. Biochem. Anal.*, 23, "The Growth and Preliminary Investigation of Protein and Nucleic Acid Crystals for X–Ray Diffraction Analysis", pp. 249–345.
Delucas et al. (1987) *Trends Biochem. Technol.*, 5, "New Directions in Prottein Crystal Growth", pp. 188–193.
Giegéet al. (1989) *Trends Biochem. Technol.*, 7, "Crystallogenesis of Proteins", pp. 277–282.

*Primary Examiner*—Robert A. Wax
*Assistant Examiner*—Nashaat T. Nashed
*Attorney, Agent, or Firm*—Amster, Rothstein & Ebenstein

[57] ABSTRACT

This invention relates to InhA enzyme crystals and to the use of said crystals to determine the three dimensional structure of InhA enzyme. This invention is further directed to a method of treating *M. tuberculosis* infection utilizing compounds which bind to InhA enzyme.

1 Claim, 1 Drawing Sheet

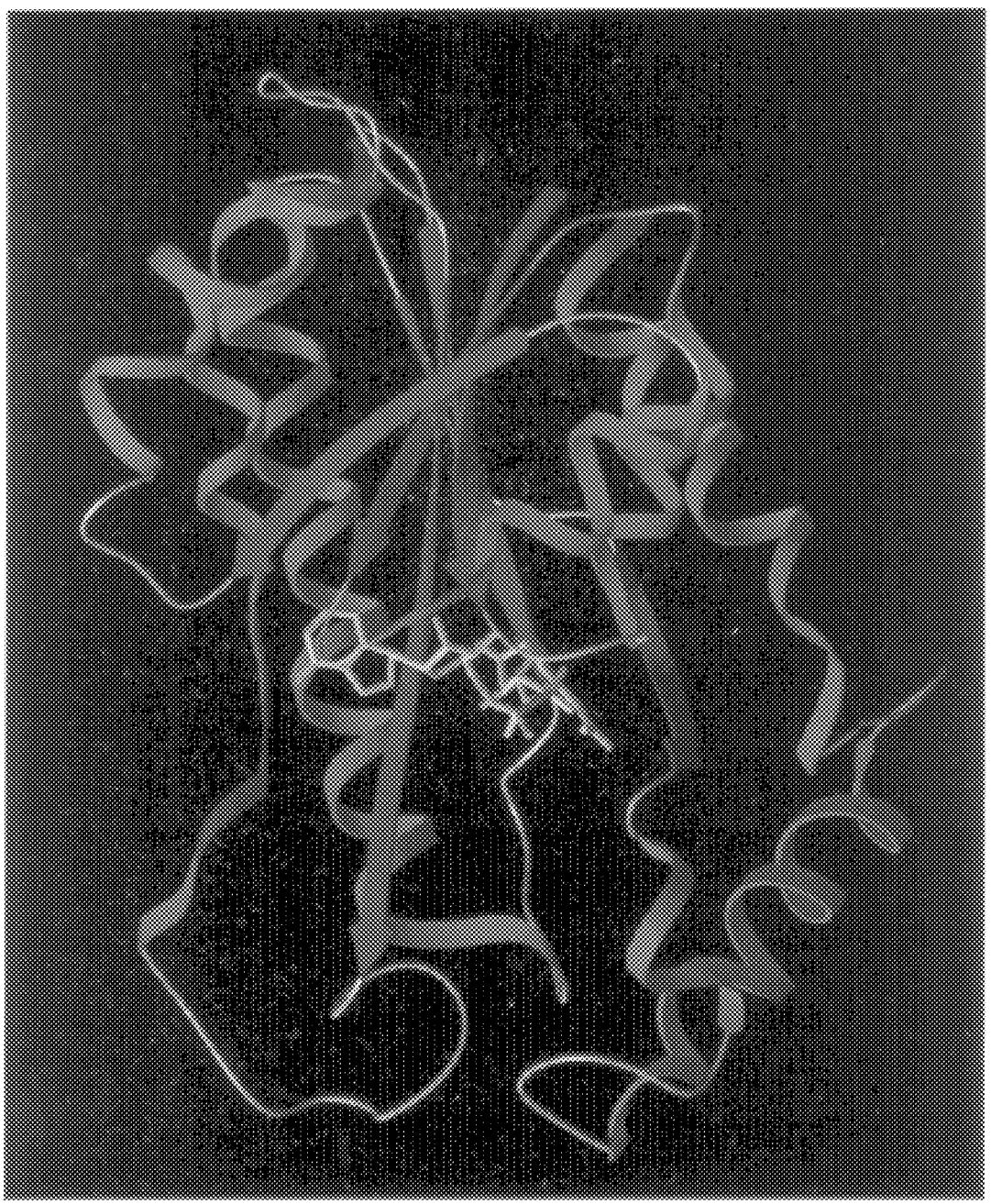

INHA CRYSTALS AND THREE DIMENSIONAL STRUCTURE

This is a divisional of application Ser. No. 08/491,146 filed on Jun. 16, 1995, now U.S. Pat. No. 5,556,778 which is a continuation of Ser. No. 08/307,376, filed Sep. 16, 1994 now abandoned, which itself is a CIP of Ser. No. 08/234,011, filed Apr. 28, 1994, now U.S. Pat. No. 5,702,935. +gi

STATEMENT OF GOVERNMENT INTEREST

This invention was made with government support under NIH Grant Numbers AI33696 and AI27160. As such, the government has certain rights in the invention.

FIELD OF THE INVENTION

This invention is directed to InhA enzyme crystals, to the use of said InhA enzyme crystals to determine the three dimensional structure of InhA enzyme and to the three dimensional structure of said InhA enzyme. The three dimensional structure of the InhA enzyme allows for the development of compounds which inhibit the biochemical activity of InhA enzyme in bacteria. Said compounds are developed and administered to treat bacterial infection.

BACKGROUND OF THE INVENTION

Tuberculosis remains the largest cause of death in the world from a single infectious disease and is responsible for one in four avoidable adult deaths in developing countries. Infection with drug-sensitive strains of *Mycobacterium tuberculosis* can be effectively cured with a combination of isoniazid, ethionamide, rifampicin and pyrazinamide. However, the emergence of multiple drug resistant strains of *M. tuberculosis* has resulted in fatal outbreaks in the United States.

Isoniazid was first reported to be active against *M. tuberculosis* in 1952, when it was shown to have a highly specific activity against *M. tuberculosis* and *M. bovis*, with less but considerable activity against other mycobacteria. Although isoniazid is one of the most widely used anti-tuberculosis drugs for both therapy and prophylaxis, its precise target of action on *Mycobacterium tuberculosis* has remained unknown. Isoniazid was first synthesized as an organic compound in 1912, but it was not until 1952 that three independent groups discovered that it had anti-tuberculosis activity. The discovery that ethionamide had anti-tuberculosis activity was predicated on the discovery that nicotinamide showed some tuberculostatic activity against *M. tuberculosis*.

Resistance to isoniazid was first reported in 1953, but in recent years has been as high as 26% in some areas of the United States. A fraction of isoniazid-resistant strains had been shown to be associated with a loss of catalase activity (see Lefford et al., *Tubercle*, Vol. 47, p. 109 (1966) and Stoecle et al., *J. Inf. Dis.*, Vol. 168, p. 1063 (1993)). The catalase gene (katG) was recently cloned and deletions of this gene were shown to be correlated with isoniazid resistance in certain *M. tuberculosis* isolates (see Zhang et al., *Nature*, Vol. 358, pp. 591–593 (1992)). Furthermore, transfer of the *M. tuberculosis* katG gene to isoniazid-resistant *M. smegmatis* strains results in the acquisition of isoniazid-sensitivity, suggesting that the presence of the catalase activity results in the sensitivity of *M. tuberculosis* to isoniazid (see Middlebrook, *Am. Rev. Tuberc.*, Vol. 65, pp. 765–767 and Zhang et al., *Molec. Microbiol.*, Vol. 8, pp. 521–529 (1993)).

Although catalase may be important to the action of isoniazid, it does not appear to be the target of action of the drug. Isoniazid-resistance can be accounted for by the loss of catalase activity; however, only 25% of isoniazid-resistant isolates appear to be catalase-negative. Previous studies have shown that low-level isoniazid resistance correlated not with the loss of catalase activity, but rather with the co-acquisition of ethionamide resistance (see Canetti, *Am. Rev. Respir. Dis.*, Vol. 92, p. 687 (1965); Grumbach, *Rev. Tuber.*, Vol. 25, p. 1365 (1961); Lefford, *Tubercle*, Vol. 47, p. 198 (1966) and Hok, *Am. Rev. Respir. Rev.*, Vol. 90, pp. 468–469 (1964)).

Drug resistance can often be mediated by the accumulation of mutations in the gene encoding the targets that result in reduced binding of drugs to their targets. For example, rifampicin resistance is often mediated by mutations in the gene encoding the β' subunit of RNA polymerase. Alternatively, trimethoprim resistance can be mediated by mutations causing amplification in a target dihydrofolate reductase.

Without the availability of genetic systems for the mycobacteria, the identification of the precise target of action of isoniazid and ethionamide could not be determined. Hence, it has been desirable to identify the specific point mutations that confer resistance to isoniazid and ethionamide in *M. tuberculosis*. The enzyme which is the target of action of isoniazid has been identified and denoted as InhA, and the gene which encodes the enzyme InhA has been denoted inhA (see Banerjee et al., *Science*, Vol. 263, pp. 227,230 (Jan, 1994)). As used herein, "InhA" includes InhA enzyme and any mutants thereof.

The inhA gene shares significant homology with a gene which codes for the EnvM protein from *E. coli* and *Salmonella typhimurium*, which is known to be involved in fatty acid (lipid or mycolic acid) biosynthesis. The enzyme InhA, encoded by the inhA gene, is necessary for mycolic acid biosynthesis.

Mycolic acids, also referred to herein as lipids, are long chain fatty acids (60 to 80 carbons in lengths) that are major constituents of a mycobacterial cell wall. They are thought to be the chemical moeities responsible for the characteristic acid-fastness of mycobacteria and form the waxy layer of mycobacterial cells. Mycolic acids have been demonstrated to have covalent linkages to arabino-galactans and thus maintain the integrity of the mycobacterial cell wall. Inhibition in their syntheses would result in a disruption of the cell wall and the death of the mycobacteria. Since mycolic acids are unique to the mycobacteria, mycolic acid biosynthetic enzymes are excellent targets for development of drugs of use in the treatment of mycobacterial infection. However, in order to develop drugs capable of inhibiting InhA activity, it is necessary to have InhA crystals from which the three dimensional structure of InhA enzyme can be determined.

It is therefore an object of this invention to provide InhA enzyme crystals.

It is another object of this invention to provide a method of determining the three dimensional structure of InhA enzyme utilizing said crystals.

It is a further object of this invention to provide the three dimensional structure of InhA enzyme.

It is a still further object of this invention to provide a method of treating mycobacterial infection utilizing compounds which block the biochemical activity of InhA enzyme.

SUMMARY OF THE INVENTION

This invention is directed to an isolated InhA enzyme comprising a first sub-structure which is a core α/β structure composed of six parallel β strands surrounded and interwoven by four α-helices and a second sub-structure composed of two α-helices interconnected by a loop. This invention is further directed to a method of determining the three dimensional structure of the InhA enzyme by determining the structure of InhA crystals utilizing multiple isomorphous replacement, and developing a polyalanine model of the crystals, thereby obtaining the three dimensional structure of the crystals.

In addition, this invention is directed to a method of treating M. tuberculosis infection comprising the determination of the three dimensional structure of InhA enzyme from M. tuberculosis, utilization of said three dimensional structure to develop a compound which binds to said enzyme and contacting said compound with said enzyme, thereby inhibiting the biochemical activity of said enzyme and treating M. tuberculosis infection.

BRIEF DESCRIPTION OF THE DRAWING

The file of the patent contains at least one drawing executed in color. The above brief description, as well as further objects and features of the present invention, will be more fully understood by reference to the following detailed description of the presently preferred, albeit illustrative, embodiments of the present invention when taken in conjunction with the accompanying drawing wherein:

FIG. 1 represents a ribbon strand diagram of the three dimensional structure of InhA enzyme from M. tuberculosis.

DETAILED DESCRIPTION OF THE INVENTION

InhA enzyme was overexpressed in a commercially available E. coli system and purified utilizing the nucleic acid sequence of InhA. The DNA sequence encoding InhA is as follows:

SEQ ID NO: 1

| | | | | | | |
|---|---|---|---|---|---|---|
| AGCGCGACAT | ACCTGCTGCG | CAATTCGTAG | GGCGTCAATA | CACCCGCAGC | CAGGGCCTCG | 60 |
| CTGCCCAGAA | AGGGATCCGT | CATGGTCGAA | GTGTGCTGAG | TCACACCGAC | AAACGTCACG | 120 |
| AGCGTAACCC | CAGTGCGAAA | GTTCCCGCCG | GAAATCGCAG | CCACGTTACG | CTCGTGGACA | 180 |
| TACCGATTTC | GGCCCGGCCG | CGGCGAGACG | ATAGGTTGTC | GGGGTGACTG | CCACAGCCAC | 240 |
| TGAAGGGGCC | AAACCCCCAT | TCGTATCCCG | TTCAGTCCTG | GTTACCGGAG | GAAACCGGGG | 300 |
| GATCGGGCTG | GCGATCGCAC | AGCGGCTGGC | TGCCGACGGC | CACAAGGTGG | CCGTCACCCA | 360 |
| CCGTGGATCC | GGAGCGCCAA | AGGGGCTGTT | TGGCGTCGAA | TGTGACGTCA | CCGACAGCGA | 420 |
| CGCCGTCGAT | CGCGCCTTCA | CGGCGGTAGA | AGAGCACCAG | GGTCCGGTCG | AGGTGCTGGT | 480 |
| GTCCAACGCC | GGCCTATCCG | CGGACGCATT | CCTCATGCGG | ATGACCGAGG | AAAAGTTCGA | 540 |
| GAAGGTCATC | AACGCCAACC | TCACCGGGGC | GTTCCGGGTG | GCTCAACGGG | CATCGCGCAG | 600 |
| CATGCAGCGC | AACAAATTCG | GTCGAATGAT | ATTCATAGGT | TCGGTCTCCG | GCAGCTGGGG | 660 |
| CATCGGCAAC | CAGGCCAACT | ACGCAGCCTC | CAAGGCCGGA | GTGATTGGCA | TGGCCCGCTC | 720 |
| GATCGCCCGC | GAGCTGTCGA | AGGCAAACGT | GACCGCGAAT | GTGGTGGCCC | CGGGCTACAT | 780 |
| CGACACCGAT | ATGACCCGCG | CGCTGGATGA | GCGGATTCAG | CAGGGGGCGC | TGCAATTTAT | 840 |
| CCCAGCGAAG | CGGGTCGGCA | CCCCCGCCGA | GGTCGCCGGG | GTGGTCAGCT | TCCTGGCTTC | 900 |
| CGAGGATGCG | AGCTATATCT | CCGGTGCGGT | CATCCCGGTC | GACGGCGGCA | TGGGTATGGG | 960 |
| CCACTGACAC | AACACAAGGA | CGCACATGAC | AGGACTGCTG | GACGGCAAAC | GGATTCTGGT | 1020 |
| TAGCGGAATC | ATCACCGACT | CGTCGATCGC | GTTTCACATC | GCACGGGTAG | CCCAGGAGCA | 1080 |
| GGGCGCCCAG | CTGGTGCTCA | CCGGGTTCGA | CCGGCTGCGG | CTGATTCAGC | GCATCACCGA | 1140 |
| CCGGCTGCCG | GCAAAGGCCC | CGCTGCTCGA | ACTCGACGTG | CAAAACGAGG | AGCACCTGGC | 1200 |

-continued
SEQ ID NO: 1

```
CAGCTTGGCC GGCCGGGTGA CCGAGGCGAT CGGGGCGGGC AACAAGCTCG ACGGGGTGGT 1260

GCATTCGATT GGGTTCATGC CGCAGACCGG GATGGGCATC AACCCGTTCT TCGACGCGCC 1320

CTACGCGGAT GTGTCCAAGG GCATCCACAT CTCGGCGTAT TCGTATGCTT CGATGGCCAA 1380

GGCGCTGCTG CCGATCATGA ACCCCGGAGG TTCCATCGTC GGCATGGACT TCGACCCGAG 1440

CCGGGCGATG CCGGCCTACA ACTGGATGAC GGTCGCCAAG AGCGCGTTGG AGTCGGTCAA 1500

CAGGTTCGTG GCGCGCGAGG CCGGCAAGTA CGGTGTGCGT TCGAATCTCG TTGGCGCAGG 1560

CCCTATCCGG ACGCTGGCGA TGAGTGCGAT CGTCGGCGGT GCGCTCGGCG AAGAGGCCGG 1620

CGCCCAGATC CAGCTGCTCG AGGAGGGCTG GGATCAGCGC GCTCCGATCG GCTGGAACAT 1680

GAAGGATGCG ACGCCGGTCG CCAAGACGGT GTGCGCGCTG CTGTCTGACT GGCTGCCGGC 1740

GACCACGGGT GACATCATCT ACGCCGACGG CGGCGCGCAC ACCCAATTGC TCTAGAACGC 1800

ATGCAATTTG ATGCCGTCCT GCTGCTGTCG TTCGGCGGAC CGGAAGGGCC CGAGCAGGTG 1860

CGCCCGTTCC TGGAGAACGT TACCCGGGGC CGCGGTGTGC CTGCCGAACG GTTGGACGCG 1920

GTGGCCGAGC ACTACCTGCA TTTCGGTGGG GTATCACCGA TCAATGGCAT TAATCGCACA 1980

CTGATCGCGG AGCTGGAGGC GCAGCAAGAA CTGCCGGTGT ACTTCGGTAA CCGCAACTGG 2040

GAGCCGTATG TAGAAGATGC CGTTACGGCC ATGCGCGACA ACGGTGTCCG GCGTGCAGCG 2100

GTCTTTGCGA CATCTGCGTG GAGCGGTTAC TCGAGCTGCA CACAGTACGT GGAGGACATC 2160

GCGCGGCCCC CCGCGCGGCC GGGCGCGACG CGCCTGAACT GGTAAAACTG CGGCCCTACT 2220

TCGACCATCC GCTGTTCGTC GAGATGTTCG CCGACGCCAT CACCGCGGCC GCCGCAACCG 2280

TGCGCGGTGA TGCCCGGCTG GTGTTCACCG CGCATTCGAT CCCGACGGCC GCCGACCGCC 2340

GCTGTGGCCC CAACCTCTAC AGCCGCCAAG TCGCCTACGC CACAAGGCTG GTCGCGGCCG 2400

CTGCCGGATA CTGCGACTTT GACCTGGCCT GGCAGTCGAG ATCGGGCCCG CCGCAGGTGC 2460

CCTGGCTGGA GCCAGACGTT ACCGACCAGC TCACCGGTCT GGCTGGGGCC GGCATCAACG 2520

CGGTGATCGT GTGTCCCATT GGATTCGTCG CCGACCATAT CGAGGTGGTG TGGGATCTCG 2580

ACCACGAGTT GCGATTACAA GCCGAGGCAG CGGGCATCGC GTACGCCCGG GCCAGCACCC 2640

CCAATGCCGA CCCGCGGTTC GCTCGACTAG CCAGAGGTTT GATCGACGAA CTCCGTTACG 2700

GCCGTATACC TGCGCGGGTG AGTGGCCCCG ATCCGGTGCC GGGCTGTCTG TCCAGCATCA 2760

ACGGCCAGCC ATGCCGTCCG CCGCACTGCG TGGCTAGCGT CAGTCCGGCC AGGCCGAGTG 2820

CAGGATCGCC GTGACCGCGG ACATCCGGGC CGAGCGCACC ACGGCGGTCA ACGGTCTCAA 2880
```

-continued
SEQ ID NO: 1

```
CGCATCGGTG GCACGCTGAG CGTCCGACAA CGACTGCGTT CCGATCGGCA ATCGACTCAG 2940

CCCGGCACTG ACCGCGATGA TCGCATCGAC GTGCGCGGCA TTCTCGAGCA CCCGCAATGC 3000

GCGCGATGGC GCGTGGTCGG GAACCCGGTG TTGCCGTGAC GATTCGAGCA ACTGCTCGAC 3060

GAGGCCACGG GGCTTGGCGA CGTCGCTAGA TCCCAGTCCG ATGGTGCTCA AGGCTTCGGC 3120
```

In order to determine the three dimensional structure of InhA enzyme, recombinant InhA from M. tuberculosis was purified. The InhA:β-Nicotinamide adenine dinucleotide, reduced and oxidized (NADH) complex was crystallized by the hanging drop vapor diffusion method, where 3 μl of protein solution (13 mg/ml InhA, in a 1:2 ratio with NADH) were mixed with 3 μl or precipitant solution (50 mM HEPES pH 7.2, 8–12% methyl pentane diol (MPD), 50 mM sodium citrate pH 6.2) on a silanized coverslip which was inverted and sealed above 700 μl of the precipitant solution.

Single crystals of up to 0.6 mm$^3$ in size were grown in this way at 19° C. within three weeks. The crystals were hexagonal in shape and were of the space group P6$_2$22. The InhA crystals grown had unit cell dimensions of a=b=100.1 Å, c=140.4 Å, and α=β=90°, γ=120°. There was one monomer per asymmetric unit, and the solvent content of the crystals was approximately 60%. Two heavy atom derivatives (p-(chloromercury)- phenyl sulfonate (PCMPS), and Hg(C$_2$H$_3$O$_2$)) were prepared and used to determine the three dimensional structure of the crystals.

A mercury acetate derivative of the crystals was collected after a native crystal (containing NADH) was soaked overnight in 1 mM C2H3O2 Hg and 10% MPD, 50 mM HEPES pH 7.2, 50 mM Na-citrate pH 6.2. The PCMPS derivative was obtained by pre-reacting the protein (13 mg/ml in 10 mM HEPES, pH 7.2, with 1:2 ratio with NADH) with 10 mM PCMPS for approximately 30 minutes at 19° C. and then crystallizing the complex under the same conditions that gave native crystals. Crystals of the InhA complex were hexagonal and isomorphous with the native form and were used in multiple isomorphous replacement (MIR) procedures to determine the three dimensional structure of the InhA enzyme.

Heavy derivatives (PCMPS, mercury acetate, and lead acetate) of the P6$_2$22 crystals of InhA were used to determine the three dimensional structure of InhA. The lead derivative was collected after a native crystal, originally produced in the presence of a 2:1 NADH:protein ratio, was soaked overnight in 1 mM C$_4$H$_6$O$_4$Pb in 0.1M Na acetate, 0.1M Na HEPES, 10% MPD (methyl pentane diol), pH 6.5. The mercury derivative was collected after a native crystal grown in the same fashion was soaked overnight in 1 mM C$_4$H$_6$O$_4$Hg in 0.1 Na citrate, 0.1M Na HEPES, 10% MPD, pH 7.2. The PCMPS derivative was obtained by mixing the protein (10 mg/mL in 10 mM HEPES, pH 7.2) with a 6-fold molar excess of PCMPS overnight at 19° C. and then crystallizing the complex under the same conditions that gave native crystals. A heavy atom derivative of InhA with PCMPS can also be obtained by utilizing the same procedure as in the lead acetate experiment, but with lower metal occupancy. Crystals of the InhA-PCMPS were hexagonal with the native form and were used in the MIR procedures.

Heavy atom binding positions were found using Patterson maps. The heavy atom binding positions (as calculated from difference Patterson maps) were refined by an iterative series of phase refinement, using the package PHASES (W. Furey, VA Medical School and University of Pittsburgh, Pa.), and XtalView (see McRee et al. (1993)), running on a Silicon Graphics Iris computer. Solvent flattening (Wang, 1985) procedures, as implemented in PHASES, were used to further improve the MIR phases. From the resulting electron density map (up t 2.8 Å), a partial model of InhA was built.

All data sets were collected on a Siemens multiwire area detector, using a Rigaku RU-200 rotating anode X-ray source operating at 55 kV and 85 mA. Data were reduced using the Siemens package XENGEN (Siemens Analytica X-ray Instruments, Inc., Madison, Wis.) on a Silicon Graphics Iris computer. For the native data set, the R-merge on intensities was 9.6% to 2.2 Å for 23880 reflections (81% complete). The PCMPS derivative had an R-merge on intensities of 13.9% for 26375 reflections to 2.5 Å resolution. The HG(C$_2$H$_3$O$_2$) derivative had an R-merge on intensities of 14.3% for 26261 reflections at 2.5 Å resolution.

The three dimensional structure of InhA was determined using multiple isomorphous replacement data collected from the derivatives. Table 1, below, summarizes the statistics for phase determination.

TABLE 1

HEAVY ATOM DERIVATIVES OF INHA
FROM MYCOBACTERIUM TUBERCULOSIS

| HEAVY ATOM | CON-CENT | $R_{sym}$ | $R_{merge}$ | EXT. Diffr. (Å) | N° SITES | PHASING POWER |
|---|---|---|---|---|---|---|
| Hg(C$_2$H$_3$O$_2$)$_2$ | 1 mM | 0.143 | 0.106 | 2.5 | 1 | 1.55 |
| PCMPS CO-CRYSTAL | 2 mM | 0.139 | 0.107 | 2.5 | 4 | 1.60 |

Data produced a mean figure of merit of 0.499 for 11061 phased reflections with F>1τ. Solvent flattening (Wang, 1985) procedures, as implemented in PHASES, were used to further improve the MIR phases. From the resulting electron density map, a partial polyalanine model was built using the program TOM, a derivative of FRODO (Jones, 1985), displayed on an Iris Graphics workstation.

The polyalanine model was refined using molecular dynamics and energy minimization (see Brunger et al. (1987)). In the first step, the simulated annealing procedure "slow cool" (see Brunger (1992)) was used. Electron density maps (both 2|F$_o$–F$_c$|and|F$_o$–F$_c$|) were calculated using the atomic coordinates of the polyalanine model. Subsequently, the use of a combination of the MIR map and combined maps (maps obtained combining model-based and MIR phases) allowed for the tracing of the complete model and the incorporation of the complete amino acid sequence, as well as the bound NADH moiety.

It was determined by the inventors that recombinant InhA from *M. tuberculosis* is a single-domain enzyme, shown as a ribbon strands diagram in FIG. 1. Two substructures can be identified in the protein. The first substructure is a core α/β structure composed of six parallel β strands surrounded and interwoven by four α-helices, harboring the N-terminal section of the macromolecule. The second substructure is a C-terminal region, composed mainly of two α-helices interconnected by a short loop. The topology of substructure 1 emulates that of the dinucleotide binding fold of many dehydrogenases in that it contains a twisted β-sheet in the middle, surrounded by α-helices.

This substructure can be divided into two sections. The first section consists of two β strands (B-1 and B-2) and two short α-helices (A-1 and A-2). This section is connected to the second section of the fold by a third β strand (B-3), which crosses over to the other side of the structure. The second part of the fold consists of an α-helix (A-3), connected by a long loop to the 4th 14-residue β strand (B-4). A fourth α-helix (A-4) connects into a fifth β strand (B-5), which is followed by a 25-residue α-helix (A-5). This structure then connects into a sixth β strand (B-6), which is the last secondary structural motif in the nucleotide binding fold. The second part of the nucleotide-binding fold is unusual in that the helices are of very long nature. The longest α-helix, A-5, may be interacting with the carboxyl terminal helices.

A short loop connects the nucleotide binding fold to the carboxyl terminal domain, which consists of a short β strand (B-7) followed by two helices (A-6 and A-7) interconnected by a 5-residue loop. The C-terminal portion of the molecule consists of two other α-helical structures.

The active site of InhA lies on a cavity on the surface of the molecule, formed by the carboxyl termini of the β sheets which participate in the α/β core and two α-helices, A-5 and A-6. NADH lies in an extended conformation along the top of the carboxyl termini of the core sheet, in a binding manner which is commonly observed in dinucleotide binding enzymes. The substrate binding site is in the hydrophobic cavity composed of helices 4, 5 and 6, which are highly rich in hydrophobic residues. The hydrophobic nature of this cavity likely renders it optimal for the accommodation of the lipid substrate in close proximity to the nicotinamide moiety of NADH. It is also likely that the three aforementioned helices form a core which acts as a flexible diaphragm which expands upon substrate binding.

The three dimensional structure of InhA enzyme can be utilized to develop compounds which bind to InhA enzyme thereby inhibiting the biochemical activity of InhA enzyme, such as mycolic acid biosynthesis. Specifically, compounds can be designed which bind to the active site and/or the NADH region on the InhA enzyme to inhibit the biochemical activity of the InhA enzyme. Hence, the compounds which are developed utilizing the three dimensional structure of InhA enzyme can be administered to treat *M. tuberculosis* infection.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method for identifying a potential inhibitor of InhA enzyme comprising the following steps:

(a) obtaining a hexagonal shape crystal of the InhA enzyme of space group $P6_222$ having unit cell constants of a=b=100.1 Å, c=140.4 Å, and $\alpha=\beta=90°$, y=120° with one monomer per asymmetric unit;

(b) obtaining the atomic coordinates of the InhA enzyme by x-ray defraction studies using the crystal of (a);

(c) using the atomic coordinates of (b) to define the catalytic active site of the InhA enzyme;

(d) identifying a compound that fits the active site of (c);

(e) obtaining the compound; and (f) contacting the compound with the InhA enzyme in the presence of a substrate in solution to determine the inhibition of the enzymatic activity by said compound.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 3120
        ( B ) TYPE: nucleic acid
        ( C ) STRANDEDNESS: single
        ( D ) TOPOLOGY: both ( i i ) MOLECULE TYPE: DNA
        ( A ) DESCRIPTION:

( i i i ) HYPOTHETICAL: No ( i v ) ANTI-SENSE:

( v ) FRAGMENT TYPE:

( v i ) ORIGINAL SOURCE: inhA operon
        ( A ) ORGANISM: M tuberculosis
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE: M tuberculosis ( v i i i ) POSITION IN GENOME:

(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION: None
(A) AUTHORS:
(B) TITLE:
(C) JOURNAL:
(D) VOLUME:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 1:

```
AGCGCGACAT ACCTGCTGCG CAATTCGTAG GGCGTCAATA CACCCGCAGC CAGGGCC      60
CTGCCCAGAA AGGGATCCGT CATGGTCGAA GTGTGCTGAG TCACACCGAC AAACGT      120
AGCGTAACCC CAGTGCGAAA GTTCCCGCCG GAAATCGCAG CCACGTTACG CTCGTG      180
TACCGATTTC GGCCCGGCCG CGGCGAGACG ATAGGTTGTC GGGGTGACTG CCACAG      240
TGAAGGGGCC AAACCCCCAT TCGTATCCCG TTCAGTCCTG GTTACCGGAG GAAACC      300
GATCGGGCTG GCGATCGCAC AGCGGCTGGC TGCCGACGGC CACAAGGTGG CCGTCA      360
CCGTGGATCC GGAGCGCCAA AGGGGCTGTT TGGCGTCGAA TGTGACGTCA CCGACA      420
CGCCGTCGAT CGCGCCTTCA CGGCGGTAGA AGAGCACCAG GGTCCGGTCG AGGTGC      480
GTCCAACGCC GGCCTATCCG CGGACGCATT CCTCATGCGG ATGACCGAGG AAAAGT      540
GAAGGTCATC AACGCCAACC TCACCGGGGC GTTCCGGGTG GCTCAACGGG CATCGC      600
CATGCAGCGC AACAAATTCG GTCGAATGAT ATTCATAGGT TCGGTCTCCG GCAGCT      660
CATCGGCAAC CAGGCCAACT ACGCAGCCTC CAAGGCCGGA GTGATTGGCA TGGCCC      720
GATCGCCCGC GAGCTGTCGA AGGCAAACGT GACCGCGAAT GTGGTGGCCC CGGGCT      780
CGACACCGAT ATGACCCGCG CGCTGGATGA GCGGATTCAG CAGGGGGCGC TGCAAT      840
CCCAGCGAAG CGGGTCGGCA CCCCCGCCGA GGTCGCCGGG GTGGTCAGCT TCCTGG      900
CGAGGATGCG AGCTATATCT CCGGTGCGGT CATCCGGTC GACGGCGGCA TGGGTA      960
CCACTGACAC AACACAAGGA CGCACATGAC AGGACTGCTG GACGGCAAAC GGATT     1020
TAGCGGAATC ATCACCGACT CGTCGATCGC GTTTCACATC GCACGGGTAG CCCAG     1080
GGGCGCCCAG CTGGTGCTCA CCGGGTTCGA CCGGCTGCGG CTGATTCAGC GCATC     1140
CCGGCTGCCG GCAAAGGCCC CGCTGCTCGA ACTCGACGTG CAAAACGAGG AGCAC     1200
CAGCTTGGCC GGCCGGGTGA CCGAGGCGAT CGGGCGGGC AACAAGCTCG ACGGG     1260
GCATTCGATT GGGTTCATGC CGCAGACCGG GATGGGCATC AACCCGTTCT TCGAC     1320
CTACGCGGAT GTGTCCAAGG GCATCCACAT CTCGGCGTAT TCGTATGCTT CGATG     1380
GGCGCTGCTG CCGATCATGA ACCCCGGAGG TTCCATCGTC GGCATGGACT TCGAC     1440
CCGGGCGATG CCGGCCTACA ACTGGATGAC GGTCGCCAAG AGCGCGTTGG AGTCG     1500
CAGGTTCGTG GCGCGCGAGG CCGGCAAGTA CGGTGTGCGT TCGAATCTCG TTGGC     1560
CCCTATCCGG ACGCTGGCGA TGAGTGCGAT CGTCGGCGGT GCGCTCGGCG AAGAG     1620
CGCCCAGATC CAGCTGCTCG AGGAGGGCTG GGATCAGCGC GCTCCGATCG GCTGG     1680
```

-continued

| | | | | | | |
|---|---|---|---|---|---|---|
| GAAGGATGCG | ACGCCGGTCG | CCAAGACGGT | GTGCGCGCTG | CTGTCTGACT | GGCTG | 1740 |
| GACCACGGGT | GACATCATCT | ACGCCGACGG | CGGCGCGCAC | ACCCAATTGC | TCTAG | 1800 |
| ATGCAATTTG | ATGCCGTCCT | GCTGCTGTCG | TTCGGCGGAC | CGGAAGGGCC | CGAGC | 1860 |
| CGCCCGTTCC | TGGAGAACGT | TACCCGGGGC | CGCGGTGTGC | CTGCCGAACG | GTTGG | 1920 |
| GTGGCCGAGC | ACTACCTGCA | TTTCGGTGGG | GTATCACCGA | TCAATGGCAT | TAATC | 1980 |
| CTGATCGCGG | AGCTGGAGGC | GCAGCAAGAA | CTGCCGGTGT | ACTTCGGTAA | CCGCA | 2040 |
| GAGCCGTATG | TAGAAGATGC | CGTTACGGCC | ATGCGCGACA | ACGGTGTCCG | GCGTG | 2100 |
| GTCTTTGCGA | CATCTGCGTG | GAGCGGTTAC | TCGAGCTGCA | CACAGTACGT | GGAGG | 2160 |
| GCGCGGCCCC | CCGCGCGGCC | GGGCGCGACG | CGCCTGAACT | GGTAAAACTG | CGGCC | 2220 |
| TCGACCATCC | GCTGTTCGTC | GAGATGTTCG | CCGACGCCAT | CACCGCGGCC | GCCGC | 2280 |
| TGCGCGGTGA | TGCCCGGCTG | GTGTTCACCG | CGCATTCGAT | CCCGACGGCC | GCCGA | 2340 |
| GCTGTGGCCC | CAACCTCTAC | AGCCGCCAAG | TCGCCTACGC | CACAAGGCTG | GTCGC | 2400 |
| CTGCCGGATA | CTGCGACTTT | GACCTGGCCT | GGCAGTCGAG | ATCGGGCCCG | CCGCA | 2460 |
| CCTGGCTGGA | GCCAGACGTT | ACCGACCAGC | TCACCGGTCT | GGCTGGGGCC | GGCAT | 2520 |
| CGGTGATCGT | GTGTCCCATT | GGATTCGTCG | CCGACCATAT | CGAGGTGGTG | TGGGA | 2580 |
| ACCACGAGTT | GCGATTACAA | GCCGAGGCAG | CGGGCATCGC | GTACGCCCGG | GCCAG | 2640 |
| CCAATGCCGA | CCCGCGGTTC | GCTCGACTAG | CCAGAGGTTT | GATCGACGAA | CTCCG | 2700 |
| GCCGTATACC | TGCGCGGGTG | AGTGGCCCCG | ATCCGGTGCC | GGGCTGTCTG | TCCAG | 2760 |
| ACGGCCAGCC | ATGCCGTCCG | CCGCACTGCG | TGGCTAGCGT | CAGTCCGGCC | AGGCC | 2820 |
| CAGGATCGCC | GTGACCGCGG | ACATCCGGGC | CGAGCGCACC | ACGGCGGTCA | ACGGT | 2880 |
| CGCATCGGTG | GCACGCTGAG | CGTCCGACAA | CGACTGCGTT | CCGATCGGCA | ATCGA | 2940 |
| CCCGGCACTG | ACCGCGATGA | TCGCATCGAC | GTGCGCGGCA | TTCTCGAGCA | CCCGC | 3000 |
| GCGCGATGGC | GCGTGGTCGG | GAACCCGGTG | TTGCCGTGAC | GATTCGAGCA | ACTGC | 3060 |
| GAGGCCACGG | GGCTTGGCGA | CGTCGCTAGA | TCCCAGTCCG | ATGGTGCTCA | AGGCT | 3120 |